United States Patent
Bobbert

(10) Patent No.: US 10,863,740 B2
(45) Date of Patent: Dec. 15, 2020

(54) VIRUCIDAL COMPOSITION

(71) Applicant: ASEPTIX RESEARCH B.V., Loenen aan de Vecht (NL)

(72) Inventor: Ilja Bobbert, Hilversum (NL)

(73) Assignee: ASEPTIX RESEARCH B.V., Loenen Aan de Vecht (NL)

( * ) Notice: Subject to any disclaimer, the term of this patent is extended or adjusted under 35 U.S.C. 154(b) by 0 days.

(21) Appl. No.: 16/255,581

(22) Filed: Jan. 23, 2019

(65) Prior Publication Data

US 2020/0229433 A1    Jul. 23, 2020

(51) Int. Cl.
*A01N 25/30*    (2006.01)
*A01N 25/34*    (2006.01)
*A01N 59/00*    (2006.01)

(52) U.S. Cl.
CPC ............ *A01N 25/30* (2013.01); *A01N 25/34* (2013.01); *A01N 59/00* (2013.01)

(58) Field of Classification Search
CPC ..................................................... A01N 25/30
See application file for complete search history.

(56) References Cited

U.S. PATENT DOCUMENTS

| | | | |
|---|---|---|---|
| 6,326,347 B1 * | 12/2001 | Gambogi | C11D 1/662 510/424 |
| 7,511,006 B2 * | 3/2009 | Shimmin | C11D 3/43 510/295 |
| 9,234,162 B2 * | 1/2016 | Pathak | C11D 1/06 |
| 10,154,950 B2 * | 12/2018 | Bobbert | A01N 25/30 |
| 2007/0184013 A1 | 8/2007 | Snyder et al. | |
| 2007/0190172 A1 | 8/2007 | Bobbert | |
| 2007/0275929 A1 | 11/2007 | Fuls et al. | |
| 2010/0331227 A1 * | 12/2010 | Papari | C11D 1/75 510/192 |
| 2014/0274973 A1 | 9/2014 | Pedersen et al. | |
| 2017/0000706 A1 * | 1/2017 | Bobbert | A01N 25/30 |
| 2017/0015946 A1 * | 1/2017 | Dkidak | C11D 3/0026 |
| 2017/0173196 A1 | 6/2017 | Sherry et al. | |
| 2018/0007895 A1 | 1/2018 | Karandikar et al. | |

FOREIGN PATENT DOCUMENTS

| | | |
|---|---|---|
| EP | 3 418 363 A1 | 12/2018 |
| WO | 2007/125101 A1 | 11/2007 |

OTHER PUBLICATIONS

Apr. 28, 2020 International Search Report issued in International Application No. PCT/EP2020/051571.

* cited by examiner

*Primary Examiner* — Devang K Thakor
(74) *Attorney, Agent, or Firm* — Oliff PLC

(57) ABSTRACT

A water-based virucidal composition suitable for disinfecting a surface contaminated with non-enveloped virus is set forth, wherein the composition comprises
alkylpolyglycoside surfactant in an amount of 0.1-5 wt. %,
amineoxide surfactant in an amount of 0.1-5 wt. %, wherein the amineoxide is a compound of the formula R1R2R3N+ O−, wherein R1 contains 8 to 18 carbon atoms and R2 and R3 each contain 1-4 carbon atoms,
alkylethercarboxylic acid surfactant in an amount of 0.1-5 wt. % alkylethercarboxylic acid surfactant wherein the alkylethercarboxylic acid surfactant is an alkylethercarboxylic acid of the formula R—O—(CH(Y)—CH$_2$—O)$_n$—CH$_2$—COOH, wherein R is an alkyl or alkylene group containing 6-16 carbon atoms, and each Y is independently selected from H or CH$_3$, n is 3-10, or a salt thereof,
hydrogen peroxide in an amount of 0.1-7 wt. %,
chelating agent in an amount of 0.01-2.0 wt. %,
less than 15 wt. % of C1-C6 alcohol, less than 0.10 wt. % of quaternary ammonium surfactants, and less than 0.1 wt. % amide surfactants, and
the composition having a pH in the range of 1.0-3.0.

20 Claims, No Drawings

VIRUCIDAL COMPOSITION

BACKGROUND

Non-enveloped viruses, such as coxsackieviruses, rotavirus, norovirus, rhinovirus, adenovirus, or poliovirus, can survive for extended periods on surfaces, while enveloped viruses, including H1N1 and human coronaviruses, remain infectious on surfaces after several days. The persistence of dried viruses is affected by various environmental conditions and factors such as heat, moisture, and the type of surface. Especially noroviruses have very high resistance levels and can remain infective for several months in a healthcare environment.

Furthermore, noroviruses are highly contagious and only 10-100 viral particles may be sufficient to infect an individual. They are transmitted primarily through the fecal-oral route, either by consumption of contaminated food or water, or by spreading directly from person to person. Vomiting creates effectively aerosols with high content of virus particles, which enter the oral mucosa or contaminate surfaces.

The small, non-enveloped viruses such as noroviruses are also highly resistant to most disinfectants. Despite the lack of a lipid envelope, these organisms have a very resistant viral capsid which is made out of protein. The protein capsid is resistant to both lipophilic disinfectants (i.e., quaternary ammonium compounds), as well as solvents (i.e., alcohols).

With the long period of survival and high resistance to environmental conditions, the high resistance to disinfectants, and the small amount needed for an infection, as few as 10 to 100 virus particles are sufficient to trigger an infection and may explain how norovirus spreads so quickly and widely.

SUMMARY

The present application relates to the field of disinfection and cleaning, more specifically to enhanced biocidal activity compositions that specifically possess high biocidal activity against non-enveloped viruses.

Alcohol-based virucidal compositions have been described.

US20070275929 describes a virucidal composition against norovirus, which contains 25-99 wt. % of a disinfecting alcohol, an organic acid, and water.

US20140274973 describes an antiviral composition containing 30 to 99 wt. % of an alcohol, an aromatic carboxylic acid and an aromatic hydroxyamide.

US20070184013 describes a virucidal composition comprising a C1-C6 alcohol, a cationic oligomer or polymer, and a proton donor. The composition generally contains at least 50 wt. % of alcohol.

Alcohol-based compositions have disadvantages, however. C1-C6 alcohols are flammable at room-temperature at levels exceeding 20-25%. Additionally, at least some of them have potential for causing eye irritation. More specifically, n-propanol is classified as causing serious eye damage with in class H318 in the Globally Harmonized Hazard Classification System (GHS), while isopropyl alcohol and ethanol are both classified as causing serious eye irritation in class H319. Due to their high volatility, alcohols may cause fumes which are detrimental to the user's respiratory tract. In addition to the above safety aspects, alcohols have a very adverse effect on many surfaces (such as linoleum, plastic composites, PVC, PMMA, rubbers, glues, painted surfaces, etc.), making their use as hard-surface cleaner not attractive.

Virucidal compositions not based on alcohol have also been described.

For example, US20070190172 describes the use of a composition containing $H_2O_2$ and a specific ethoxylated aliphatic phosphono-surfactant against non-enveloped viruses.

US20180007895 describes a multi-surface quaternary ammonium disinfectant cleaning composition that is efficacious against norovirus and provides residual sanitation. The composition has a pH in the range of 5-14.

There is need in the art for a virucidal composition that shows high virucidal activity while at the same time having a composition which is such that it can be applied without handling or usage precautions, or safety measures. There is a particular need for a composition which shows good virucidal activity when applied in an impregnated wet wipe. Impregnated wet wipes are widely used in healthcare environments, and are a rapidly growing category. However, the disinfectant norms required to pass for an EPA Pesticide registration for impregnated wet wipes ("towelettes") are very difficult to pass. The method requires one single wipe to be folded several times and be used to disinfect 10 carriers of dried virus inoculum in total.

The present application provides a composition which solves this problem.

DETAILED DESCRIPTION

The application pertains to a water-based virucidal composition suitable for disinfecting a surface contaminated with non-enveloped virus, wherein the composition comprises alkylpolyglycoside surfactant in an amount of 0.1-5 wt. %, amineoxide surfactant in an amount of 0.1-5 wt. %, wherein the amineoxide is a compound of the formula R1R2R3N+O−, wherein R1 contains 8 to 18 carbon atoms and R2 and R3 each contain 1-4 carbon atoms, alkylethercarboxylic acid surfactant in an amount of 0.1-5 wt. % alkylethercarboxylic acid surfactant wherein the alkylethercarboxylic acid surfactant is an alkylethercarboxylic acid of the formula R—O—(CH(Y)—$CH_2$—O)$_n$—$CH_2$—COOH, wherein R is an alkyl or alkylene group containing 6-16 carbon atoms, and each Y is independently selected from H or $CH_3$, n is 3-10, or a salt thereof, hydrogen peroxide in an amount of 0.1-7 wt. %, chelating agent in an amount of 0.01-2.0 wt. %, the composition having a pH in the range of 1.0-3.0, wherein the composition comprises less than 15 wt. % of C1-C6 alcohol, less than 0.10 wt. % of quaternary ammonium surfactants, and less than 0.1 wt. % amide surfactants.

It has been found that the compositions of the current application are surprisingly effective to kill non-enveloped viruses, most notably Norovirus and Feline Calici Virus (the surrogate for Norovirus for an EPA pesticide registration in the USA) in an impregnated wet wipe application. The compositions of the current application are able to pass the EPA set standards (currently the ASTM E1053 standard as amended for towelettes) for virucidal activity of wet wipes within reasonable contact times (up to 5 minutes and faster). Short (realistic) contact times are important to increase the practical usefulness of compositions in actual healthcare environments and enhance practical compliance.

The subject matter of the present application will be discussed in more detail below.

Unless specifically stated otherwise, all percentages in the present specification are weight percentages, calculated as the net weight of a substance on the weight of the composition.

Unless specifically specified otherwise, in the present specification the term alkyl refers to straight-chain and branched alkyl groups which may optionally be substituted with one or more of —OH, halogen, or aryl groups. In general, unless specified otherwise, alkyl groups in the present specification have 1-10 carbon atoms, in particular 4 to 18 carbon atoms.

Depending on the context, the term alkyl may also encompass alkylene, i.e., an alkyl group with one or more double bonds.

In the present specification the term aryl encompasses aromatic ring structures with 4-20 carbon atoms, which may or may not contain one or more heteroatoms selected from O, N, and S. Aryl groups may be substituted with one or more of —OH, halogen, and C1-C20 alkyl or alkylene.

The composition is characterized by the presence of a number of specific components, a pH in a specific range, and limitations on the presence of a number of other components. The presence of a combination of an alkylpolyglycoside surfactant, an aminoxide surfactant, and an alkylethercarboxylic acid surfactant is a key feature of the present application. If the composition contains only one or two of the surfactants, the virucidal effect will not be obtained. It is in itself surprising that the specific combination of the surfactants has influence on the virucidal effect of the composition, as the surfactants themselves are not known for virucidal activity.

The composition comprises 0.1-5 wt. % of alkylpolyglycoside surfactant, also indicated as APG. The APG used in the composition preferably comprises the saccharide or polysaccharide groups (i.e., mono-, di-, tri-, etc. saccharides) of hexose or pentose, and a fatty aliphatic group with 6 to 20 carbon atoms. In one embodiment, alkylpolyglycosides which can be used in the present application are represented by the general formula of

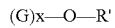

(G)x—O—R' where G is a reducing saccharide moiety containing 5 or 6 carbon atoms, e.g., pentose or hexose; R' is a straight chain or branched, in particular a straight-chain alkyl or alkylene group having 6 to 20 carbon atoms, in particular 8 to 16 carbon atoms, and x represents the number of monosaccharide repeating units in the polyglycoside, wherein x is in the range of 1 to 8, in particular in the range of 1 to 5, more in particular in the range of 1 to 3.

Exemplary saccharides from which G is derived are glucose, fructose, mannose, galactose, talose, gulose, allose, altrose, idose, arabinose, xylose, lyxose and ribose. Because of the ready availability of glucose, glucose is preferred in the making of polyglycosides. Alkylpolyglycosides based on glucose are also known as alkylpolyglucosides. Examples of commercial suppliers of alkylpolyglycosides are Dow, BASF, Seppic, Akzo Nobel, and Croda. Functionalized APGs may also be included, with cationic, amphoteric, or anionic functional groups.

The alkylpolyglycoside surfactants are present in an amount of 0.1-5 wt. %, calculated as the net weight total of one or more alkylpolyglycoside surfactants on the weight of the composition.

It may be preferred for the composition to contain 0.1 to 3 wt. % of alkylpolyglycoside surfactants, in particular 0.1-2 wt. %, in some embodiments 0.1-1.0 wt. %.

Mixtures of different alkylpolyglycoside surfactants may also be used.

The composition comprises 0.1-5 wt. % of aminoxide surfactant, wherein the aminoxide surfactant is a compound of the formula $R_1R_2R_3N^+O^-$, wherein R1 contains 8 to 18 carbon atoms and R2 and R3 each contain 1-4 carbon atoms. R1 generally is a straight-chain or branched alkyl or alkylene group, in particular a straight chain alkyl group. Examples of suitable alkyl groups are octyl, decyl, dodecyl, isododecyl, coconut, or tallow alkyl. R2 and R3 may be the same or different and generally are C1-C4 alkyl groups, in particular ethyl or methyl. Examples of suitable aminoxide surfactants are octyldimethylaminoxide, nonyldimethylaminoxide, decyldimethylaminoxide, undecyldimethylaminoxide, dodecyldimethylaminoxide, iso-dodecyldimethyl aminoxide, tridecyldimethylaminoxide, tetradecyldimethylaminoxide, pentadecyldimethylaminoxide, hexadecyldimethylaminoxide, heptadecyldimethylaminoxide, octadecyldimethylaine oxide, dodecyldipropylaminoxide, tetradecyldipropylaminoxide, hexadecyldipropylaminoxide, tetradecyldibutylaminoxide, octadecyldibutylaminoxide, bis(2-hydroxyethyl)dodecylaminoxide, bis(2-hydroxyethyl)-3-dodecoxy-1-hydroxypropylaminoxide, dimethyl-(2-hydroxydodecyl)aminoxide, 3,6,9-trioctadecyldimethylaminoxide and 3-dodecoxy-2-hydroxypropyldi-(2-hydroxyethyl)aminoxide.

The aminoxide surfactant is preferably a C8-C16, in particular a C8-C14, more in particular a C10-C12 aminoxide surfactant with R2 and R3 preferably being C1 or C2.

The aminoxide surfactants are present in an amount of 0.1-5 wt. %, calculated as the net weight of the total of one or more aminoxide surfactants on the weight of the composition. It may be preferred for the composition to contain 0.1 to 4 wt. % of aminoxide surfactant, in particular 0.1 to 3 wt. % of aminoxide surfactant, more in particular 0.1-2 wt. %. Mixtures of different aminoxide surfactants may also be used.

The composition comprises 0.1-5 wt. % of alkylethercarboxylic acid surfactant wherein the alkylethercarboxylic acid surfactant is an alkylethercarboxylic acid of the formula R—O—(CH(Y)—CH$_2$—O)$_n$—CH$_2$—COOH, wherein R is an alkyl or alkylene group containing 6-16 carbon atoms, and each Y is independently selected from H or CH$_3$, n is 3-10, or a salt thereof. Preferably, R is an alkyl or alkylene group containing 6-14 carbon atoms, more in particular 6-12 carbon atoms. Preferably R is a straight chain alkyl group. Also preferably, R is an alkyl group of 6-14 carbon atoms, more preferably of 6-8 carbon atoms. Depending on the nature of Y, the alkylethercarboxylic acid surfactant may contain ethoxy moieties, propoxy moieties or both ethoxy moieties and propoxy moieties. It is preferred for n to be in the range of 3-8. An individual compound with a structure according to Formula 1 may further contain only propoxy or only ethoxy groups or may contain a mixture of ethoxy and propoxy groups. Preferably, n is 3-8 and/or Y is H.

Preferred alkylethercarboxylic acid surfactants are compounds in which Y is H, R is a straight chain C6-C12 alkyl and n is 3-8; compounds wherein R is a straight chain C6 alkyl and n is 3-8; compounds wherein R is a straight chain C8 alkyl and n is 5-8, salts thereof, and combinations thereof. More preferred alkylethercarboxylic acid surfactants are compounds in which Y is H, R is a straight chain C6 alkyl and n is 3; compounds wherein R is a straight chain C8 alkyl and n is 8; compounds wherein R is a straight chain C8 alkyl and n is 5, and combinations thereof.

Suitable salts include soluble salts of alkali metals, earth alkali metals, and ammonia, in particular sodium salts, potassium salts, and ammonium salts.

Alkylethercarboxylic acid surfactants are commercially available. Suitable compositions include for example the surfactants marketed under the trade names AKYPO LF1, LF2, LF4 and LF6 (from KAO Chemicals).

The alkylethercarboxylic acid surfactants are present in an amount of 0.1-5 wt. %, calculated as the net total weight of one or more alkylethercarboxylic acid surfactants on the weight of the total composition.

It may be preferred for the composition to contain 0.1 to 3.0 wt. % of alkylethercarboxylic acid surfactants, in particular 0.1-2.0 wt. %, in some embodiments 0.1-1.0 wt. %. Mixtures of different alkylethercarboxylic acid surfactants may also be used.

The composition comprises 0.1-7 wt. % of hydrogen peroxide. Hydrogen peroxide is particularly attractive as a biocidal compound because its decomposition products, water and oxygen, are not toxic and not harmful to the environment. In order to provide fast, effective action, biocidal hydrogen peroxide solutions had to employ relatively high concentrations of hydrogen peroxide. However, at higher concentrations, the solutions may be subject to hazardous goods regulations and may require special precautions for handling and use. For example, at concentrations of above about 8 wt. % aqueous solution, hydrogen peroxide is considered corrosive and is also a strong oxidizing agent. Surprisingly it has been found that the use of relatively limited amounts of hydrogen peroxide can, in combination with the other compounds of the present composition, provide good antiviral activity.

The composition contains 0.1-7 wt. % of hydrogen peroxide, in particular 0.1-5 wt. %, more in particular 0.1-3 wt. %, even more in particular 0.1-2 wt. %.

The present composition comprises 0.01-2.0 wt. % of a chelating agent. It has been found that the presence of a chelating agent is necessary to obtain the effect of the present application. In general, a chelating agent is a molecule capable of coordinating (i.e., binding) the metal ions commonly found in water sources to prevent the metal ions from interfering with the action of the other ingredients. Preferred are chelating agents with a high binding affinity at low pH, and good water solubility at low pH. Examples of chelating agents include phosphonic acid and phosphonates, phosphates, aminocarboxylates and their derivatives, pyrophosphates, ethylenediamine and ethylenetriamine derivatives, hydroxyacids, and mono-, di-, and tri-carboxylates and their corresponding acids. Other chelating agents include nitroloacetates and their derivatives, and mixtures thereof, ethylenediaminetetraacetic acid (EDTA), diethylenetriaminepentaacetic acid (DTPA), N-(hydroxyethyl)-ethylenediaminetriacetic acid (HEDTA), nitrilotriacetic acid (NTA), 2-hydroxyethyliminodiacetic acid (HEIDA), and salts thereof or from benzoic acid, salicylic acid, aminobenzoic acid, citric acid, phosphoric acid, iminodisuccinic acid and polyaspartic acid. More preferably, the chelating agent is a (colloidal) stannate, and even more preferably is chosen from acetanilide, trisodium ethylenediamine disuccinate (EDDS), for instance OctaQuest E30 or A65 (Octel), derivatives of glutamic acid, such as glutamic acid diacetic acid, (tetra) sodium salt (GLDA), Iminodisuccinic acid and salts (IDS), organophosphonic acid derivatives, and its salts, having 1 to 5 phosphonic acid groups, for instance a Dequest phosphonate (Solutia), such as for example 1-hydroxyethylidene-1,1-diphosphonic acid, amino tri(methylene phosphonic acid), diethylenetriamine-penta(methylene phosphonic acid), 2-hydroxy ethylimino bis(methylene phosphonic acid), and ethylene diamine tetra(methylene phosphonic acid). The use of phosphonic acid and its derivatives is considered preferred. However, the list of chelating agents does not imply to limit the selection to these substances. It is clear to the man skilled in the art that any substance with chelating or metal-ion binding capacities may be selected.

In view of their high binding activity at low pH and good water solubility at low pH, organophosphonates, cyclic carboxylic acids, and aminopolycarboxylic acids (such as GLDA, IDS and EDDS) may be particularly preferred.

The chelating agent is present in an amount of 0.01-2.0 wt. %, calculated as the net total weight of one or more chelating agents on the weight of the composition. It may be preferred for the composition to contain 0.05-1.5 wt. % of chelating agent, in particular 0.1-1.0 wt. %. Mixtures of different chelating agents may also be used.

The composition has a pH in the range of 1.0 to 3.0. It has been found that the antiviral effect of the present composition will not be obtained when the pH is above 3.0. It may be preferred for the pH of the composition to be between 1.0 and 2.5. A pH adjusting (organic or inorganic) acid or base or an appropriate buffer may suitably be added to provide the composition of the application with the pH of choice. Suitable acids for adjusting the pH for instance are citric acid, lactic acid, phosphoric acid, sulfamic acid, nitric acid, sulfuric acid, tartaric acid, malic acid, maleic acid, etc. Suitable bases are organic and inorganic bases. Hydroxide salts such as NaOH, KOH, etc. and the associated bases of the acids used are examples of suitable compounds.

In addition to the pH and the presence of the constituents discussed above, the present composition is also characterized by limiting the presence of certain compounds.

It is a feature of the composition that it comprises less than 15 wt. % of C1-C6 alcohol, making this composition not an alcohol-based composition but a water-based composition. The disadvantages of the presence of C1-C6 alcohols have been discussed above. It is preferred for the composition to comprise less than 10 wt. % C1-C6 alcohol, in particular less than 5 wt. %. The composition may comprise less than 2 wt. % C1-C6 alcohol, or be substantially free of or free of C1-C6 alcohol.

The composition contains less than 0.10 wt. % of quaternary ammonium surfactants. The presence of quaternary ammonium surfactants is not attractive due to the low pH of the composition and the presence of anionic surfactants which may react with the positively charged quaternary ammonium compounds to form a precipitate. Furthermore, quaternary ammonium surfactant compounds are known to cause microbial resistance because they leave a residue on surfaces of a sub-minimum-inhibitory concentration. This sub-MIC level presence does not result in killing of the cells, but does cause the cell to create or activate defense mechanisms, resulting in the increasing resistance. This effect is highly undesirable. Therefore, quaternary ammonium compounds should only be used in very minimal concentrations and more preferably should not be present at all. Thus, the present composition comprises less than 0.10 wt. % of quaternary ammonium surfactants, in particular less than 0.05 wt. %. It is preferred for the composition to be substantially free or free from quaternary ammonium surfactants. In the context of the present specification, a quaternary ammonium surfactant is defined as a surfactant comprising a quaternary ammonium group and a C8-C18 alkyl or alkylene tail group.

The composition contains less than 0.1 wt. % of amide surfactant, preferably less than 0.05 wt. %, more in particular less than 0.02 wt. %. It is especially preferred for the composition to be substantially free or free from amide surfactants. Amide surfactants in the context of the present specification are surfactants composed of an alkyl tail connected to a CO—NRaRb head group, wherein Ra and Rb are H, OH, halogen, or C1-C6 alkyl. It has been found that amide surfactants have a low solubility in the composition. This would necessitate the use of increased amounts of the other surfactants used in the composition to keep the amide surfactant in solution. This is undesirable. Additionally, at the low pH values of the present composition, amide bonds are susceptible to hydrolysis, resulting in a decreased storage stability of the composition, especially at elevated temperatures. It is required for registered biocides to withstand a prolonged period of elevated temperatures to evidence stability at storage conditions in higher temperature areas, such as warehouses, ships or trucks in summer periods or warmer areas. Further, longer carbon chain (C6-C12) surfactant amides will be hydrolyzed to the C6-C12 fatty acids, which are not soluble in the composition, may precipitate and have a rancid odor. Furthermore, amides could react with nitric oxide from the air in a nitrosation reaction to form nitrosamides which are highly carcinogenic. As nitric oxide is found in air, this would exclude a spray application to be used on surfaces.

In one embodiment, the present composition comprises an organic solvent. The term solvent is intended to refer to compounds which help to dissolve organic materials such as proteins and blood.

Suitable solvents include, but are not limited to, alcohols such as ethanol, isopropanol, 2-butoxy ethanol, n-pentanol, n-propanol, 2-methylbutanol, isobutanol, n-butanol, diisobutyl carbinol 1-decanol, benzyl alcohol, phenoxyethanol, glycerin, glycols, ethylene glycol, diethylene glycol, butoxy diglycol, triethylene glycol, tetraethylene glycol, propylene glycol, dipropylene glycol, hexylene glycol, glycol ethers, esters, or combinations thereof. Suitable alcohols include, but are not limited to, ethanol, isopropanol, 2-butoxy ethanol, 1-decanol, glycerin, or any combination thereof. Alkylene glycols having from about 2 to 6 carbon atoms, straight or branched chain lower alkyl alcohols, glycerol, propylene carbonate, alkylene glycol mono alkyl ethers where the alkylene portion has from about 2 to 6 carbon atoms and the alkyl portion has about 1 to 6 carbon atoms, poly alkylene glycol mono alkyl ethers where each alkylene portion has from about 2 to 6 carbon atoms and the alkyl portion has about 1 to 6 carbon atoms, alkyl acetates where the alkyl portion has from about 1 to 6 carbon atoms, pine oil, terpenes and mixtures thereof.

Dodecane, Propylene Carbonate, Diethylene glycol mono-n-butyl ether, Isopropyl Alcohol, Butyl acetate, Glycerol, Pine Oil Hexylene Glycol, Orange oil, d-limonene or other fragrance ingredients may be present at low levels. Glycol ether solvents are commonly used in aqueous cleaning and disinfecting formulas. Glycol ethers can be formed from ethylene or propylene oxide yielding E and P series glycol ethers respectively. Examples are Propylene Glycol Methyl Ether, Dipropylene Glycol Methyl Ether, Tripropylene Glycol Methyl Ether, Propylene Glycol Methyl Ether Acetate, Dipropylene Glycol Methyl Ether Acetate, Propylene Glycol n-Propyl Ether, Dipropylene Glycol n-Propyl Ether, Propylene Glycol n-Butyl Ether, Dipropylene Glycol n-Butyl Ether, Tripropylene Glycol n-Butyl Ether, Propylene Glycol Phenyl Ether, Dipropylene Glycol Phenyl Ether, Propylene Glycol Diacetate, Dipropylene Glycol Dimethyl Ether, Diethylene Glycol Methyl Ether, Triethylene Glycol Methyl Ether, Diethylene Glycol Ethyl Ether, Triethylene Glycol Ethyl Ether, Ethylene Glycol Propyl Ether, Ethylene Glycol n-Butyl Ether, Diethylene Glycol n-Butyl Ether, Triethylene Glycol n-Butyl Ether, Ethylene Glycol n-Butyl Ether Acetate, Diethylene Glycol n-Butyl Ether Acetate, Ethylene Glycol Hexyl Ether, Diethylene Glycol Hexyl Ether, Ethylene Glycol Phenyl Ether, Diethylene Glycol Phenyl Ether.

The preferred solvent is partly or wholly water soluble, with a high capacity to solubilize organic substances, medium to fast evaporating, and having the capability to lower surface tension of an aqueous solution. In case the formulation needs to comply to VOC-regulations, the preferred solvent is medium to slow evaporating with a boiling point (in C at 760 mm Hg) of 200° C. or more, and/or a vapour pressure of <0.1 mm Hg (at 20° C.).

In view of the objections against volatile alcohols as discussed above, it is preferred not to use a C1-C6 alcohol as solvent. The use of aromatic alcohols, e.g., benzylalcohol, and the use of glycolethers may be preferred.

Solvents, if used, are preferably used in an amount of 0.1-10 wt. %, calculated as the net total weight of solvent on the weight of the composition, in particular in an amount of 0.5-8 wt. %, and in some embodiments 1.0 to 5 wt. %. Mixtures of different solvents may also be used.

The composition is a water-based composition. This means that water is present as major carrier component. In general, the composition contains at least 50 wt. % water, in particular at least 60 wt. % water, more in particular at least 70 wt. % water, even more in particular at least 80 wt. % water, still more in particular at least 85 wt. % water.

The composition may comprise further components known in the art, such as corrosion inhibitors, wetting agents, fragrances, emulsifiers, hydrotropes, thickening agents, coloring agents, preservatives, and anti-foaming agents.

The composition may comprise a corrosion inhibitor, preferably, in a concentration of 0.01% to 20% w/w. Preferably, the corrosion inhibitor is chosen from 1,2,3 benzotriazole, sodium molybdate, sodium nitrite, sodium bisulfate, sodiummetabisulfate, chromates, borates, phosphates, polyphosphates, sodium benzoate, sodium gluconate, sodium silicate and combinations thereof.

Also useful in the compositions of the application are wetting agents. Wetting agents function to increase the surface contact or penetration activity of the antimicrobial composition of the application. Wetting agents which can be used in the composition include any of those constituents known within the art to lower the surface activity of the composition. Typical super-wetters are silicone copolyols and acetylinic diols. They serve to provide wetting, leveling and spreading of the composition on difficult-to-wet substrates.

It is preferred for the composition to be substantially free or free of one or more of Triclosan, parachlorometaxylenol, biguanidines, triclocarban, phenols, and biphenols. These compounds are known for their biocidal activity, but are undesired because they are proven environmental hazardous or human toxic. Furthermore, when they are left on a surface after applying a composition comprising one or more of these substances, the residue may cause antimicrobial resistance (leaving a sub-Minimal Inhibitory Concentration) with micro-organisms.

It is furthermore preferred for the composition to be substantially free from or free from strong oxidizers such as peracetic acid, chlorine bleach, and hypochlorous acid. These compounds are known for their strong and wide-spectrum biocidal activity, but are undesired because they have a very adverse material compatibility, are instable, are human toxic (respiratory irritation, eye irritation or damage, skin corrosive), environmentally toxic, and in higher concentrations are dangerous in daily handling and use.

In one embodiment, the composition does not contain biocidally effective amounts of biocidally active compounds other than alkylpolyglycoside surfactant, amineoxide surfactant, alkylethercarboxylic acid surfactant, organic solvent, hydrogen peroxide, and chelating agent.

In the context of the present specification this means that the composition does not contain amounts of biocidally effective compounds which result in a change in a log reduction in prEN 16777 wipe test against Feline Calici Virus at two minutes contact time of more than 0.5 for each individual addition.

In one embodiment, the biocidally, in particular virucidally, active system of the composition consists essentially of
alkylpolyglycoside surfactant,
amineoxide surfactant, wherein the amineoxide is a compound of the formula R1R2R3N+O−, wherein R1 contains 8 to 18 carbon atoms and R2 and R3 each contain 1-4 carbon atoms,
alkylethercarboxylic acid surfactant wherein the alkylethercarboxylic acid surfactant is an alkylethercarboxylic acid of the formula R—O—(CH(Y)—CH$_2$—O)$_n$—CH$_2$—COOH, wherein R is an alkyl or alkylene group containing 6-16 carbon atoms, and each Y is independently selected from H or CH$_3$, n is 3-10, or a salt thereof,
hydrogen peroxide,
chelating agent, and optionally
solvent.

In the context of the present specification the term biocidally, in particular virucidally, active system refers to all elements of the composition which influence the virucidal performance of the composition, as is evidenced by a change in a log reduction in prEN 16777 wipe test against Feline Calici Virus at two minutes contact time of more than 0.5 for each individual addition.

In addition to the active system, the composition may contain further compounds such as corrosion inhibitors, wetting agents, fragrances, emulsifiers, hydrotropes, thickening agents, coloring agents, preservatives, and anti-foaming agents, again preferably so long as the additional compounds are not biocidally, or virucidally, effective compounds.

In another embodiment, the composition consists essentially of
water
alkylpolyglycoside surfactant in an amount of 0.1-5 wt. %,
amineoxide surfactant in an amount of 0.1-5 wt. %, wherein the amineoxide is a compound of the formula R1R2R3N+O−, wherein R1 contains 8 to 18 carbon atoms and R2 and R3 each contain 1-4 carbon atoms,
alkylethercarboxylic acid surfactant in an amount of 0.1-5 wt. % alkylethercarboxylic acid surfactant wherein the alkylethercarboxylic acid surfactant is an alkylethercarboxylic acid of the formula R—O—(CH(Y)—CH$_2$—O)$_n$—CH$_2$—COOH, wherein R is an alkyl or alkylene group containing 6-16 carbon atoms, and each Y is independently selected from H or CH$_3$, n is 3-10, or a salt thereof,
hydrogen peroxide in an amount of 0.1-7 wt. %,
chelating agent in an amount of 0.01-2.0 wt. %,
optionally solvent
optionally one or more compounds selected from corrosion inhibitors, wetting agents, fragrances, emulsifiers, hydrotropes, thickening agents, coloring agents, preservatives, and anti-foaming agents,
less than 15 wt. % of C1-C6 alcohol, less than 0.10 wt. % of quaternary ammonium
surfactants, and less than 0.1 wt. % amide surfactants,
the composition having a pH in the range of 1.0-3.0.

In the present specification, the term "consisting essentially of" means that no other compounds are present unless their presence cannot be reasonably avoided, e.g., as they are present as unavoidable contaminants.

A contaminant in the present specification is defined as a compound which is not intentionally added as such, but which may be present in a compound as a result of the production process. Contaminants may be present in an amount that is so small as to not materially affect the performance of the composition.

In the present specification the term "substantially free of" means that the specified compound is not present, unless its presence cannot be reasonably avoided, e.g., as it is present as unavoidable contaminants.

For example, substantially free of may encompass an amount of less than 0.05% by weight or less than 0.01% by weight, or less than 0.005% by weight.

A virucidal composition is defined as a composition which is able to achieve a reduction of the viable virus particles on a surface by at least log 2.5, in particular at least log 3.0 after contacting the surface with the composition, or the composition impregnated into a sufficiently wetted wipe, with a contact time of less than 5 minutes, preferably less than 3 minutes, most preferably less than 2 minutes, e.g., as determined in accordance with prEN 16777 or ASTM E1053.

In one embodiment, the composition shows a log reduction in prEN 16777 or the ASTM E1053 wipe test against Feline Calici Virus at three minutes contact time of at least log 2.5, in particular at least log 3.0, in particular at 2 minutes contact time.

The composition is preferably active against a non-enveloped virus selected from norovirus or its surrogate Feline Calici Virus, adenovirus, and rhinovirus, in particular norovirus or its surrogate Feline Calici Virus.

In one embodiment, the composition does not leave a biocidal or biostatic residue. Leaving a biostatic residue is defined as follows: If 6 hours after use of the composition the dried surface is able to kill germs to a minimum reduction of log 3 after contacting the surface with *E. coli, S. aureus, S. typhimurium, P. aeruginosa*, and *E. hirae* a biostatic residue is present. Leaving of a biostatic residue in not desired, because it may result in the build up of resistance in the organisms at issue.

The application also pertains to a method for disinfecting a surface suspected to be contaminated with non-enveloped virus, wherein the surface is contacted with the composition described herein, for a contact time of at most 5 minutes, in particular at most 4 minutes, more in particular at most 3 minutes.

Using the disinfectant compositions according to the application can take the form of a concentrate that can be diluted and combined to provide a ready-to-use solution, and as a ready-to-use liquid composition that can be used to clean articles having a metal, lacquered, veneered, painted, glass, or plastic surface, such as tabletops, doorknobs, floors, doors, painted surfaces, television remote controls, computer keyboards and other high touch objects that may participate in germ transmission.

Metal surfaces and/or plastic surfaces in need of disinfecting and cleaning are found in several locations. Exemplary locations include machine parts, vehicles, work surfaces, tabletops, appliance handles, lavatory surfaces, hotel room surfaces, kitchens, tables, etc. Metal surfaces that can be disinfected include iron-based metals such as iron, iron alloys, e.g., steel, tin, aluminum, copper, tungsten, titanium, molybdenum, etc., for example. The structure of the metal surface to be disinfected can vary widely. Thus, the metal surface and/or plastic surface can be as a metal and/or plastic part of complex configuration, sheeting, coils, rolls, bars, rods, plates, disks, etc.

More preferred is the use of the disinfectant cleaning composition of the application, in particular the ready-to-use composition, to disinfect coated wood, plastic, metal, glass windows and mirrors, bathtubs, shower surfaces, porcelain fixtures and the like.

The disinfectant composition can be sprayed onto a surface by an automatic sprayer, electrostatic sprayer, ultrasonic or electric fogger, high pressure system, etc.

The disinfectant composition, preferably the ready-to-use-composition, can also be applied to a surface by wiping the treated surface with a saturated cloth, mop, sponge, wet wipe, or other suitable delivery mechanism.

Especially in healthcare settings the disinfectant composition of this application is highly advantageous, being effective against non-enveloped viruses which often occur in healthcare environments. The composition can be applied by spraying, pouring or wiping surfaces such as hospital tables, beds, doorknobs, floors, medical instruments, imaging instruments, computers, keyboards, telephones, stethoscopes, ultrasonic probes, etc.

The composition can also be applied by spraying and/or flooding the surface with the disinfectant composition or by immersion of (e.g., medical) items in the use solution. A preferred method of application is to use the composition in an impregnated wet wipe. The liquid is normally allowed to keep the surface wet for the specified contact time to ensure the desired level of antimicrobial effect. The present application also pertains to a wet wipe provided with the composition according to the application.

Wet wipes are used to clean a surface though light rubbing or friction. One of the main benefits that wipes provide is convenience—using a wipe is quicker and easier than the alternative of dispensing a liquid and using another cloth/paper towel to clean or remove the liquid.

A wet wipe consists of a sheet-like substrate impregnated with a liquid composition, in the present case the composition described herein.

Suitable substrates for wet wipes are well known in the art and include woven and non-woven sheets of a fibrous material with sufficient wet strength and liquid absorption capacity to contain a suitable amount of the liquid composition according to the invention and deliver it to the surface to be cleaned. The fibers in the fibrous material may be from natural sources e.g. viscose or cellulose such as wood pulp or cotton, or cellulose fibers from paper, bamboo, wheatgrass, carton, etc. or synthetic origin such as polypropylene, (PP), Polyethylene (PE), or Polyethyleneterephtalate (PET). Combinations of materials may also be used. Optionally, the substrate may comprise one or more polymeric binders. Any binder material present should not be soluble in the liquid composition to such an extent that it causes the wipe to cause streaking on the cleaned surface.

The substrate can be manufactured by methods known in the art which require no elucidation here. The wipe may be a single layer structure or a multilayer structure, wherein the layers may be the same or different.

In one embodiment, prior to impregnation with the composition described herein, the wipe has an average thickness ranging from 0.1 to 3.0 mm, preferably from 0.2 to 1.0 mm, more preferably from 0.3 to 0.6 mm.

Prior to impregnation with the composition of the invention, the wipe typically has a base weight of from 20 to 100 $g/m^2$, preferably from 30 to 90 $g/m^2$, more preferably from 40 to 80 $g/m^2$.

The composition described herein is impregnated in a ratio of typically between 200% and 400% of liquid weight to the weight of the wipe substrate, preferably 220%-350%, depending on the material of the wipe.

As will be evident to the skilled person, it is possible to combine elements of various embodiments described above, unless they are mutually exclusive.

The subject matter of the application will be elucidated by the following examples, without being limited thereto or thereby.

Example 1

To illustrate the necessity of the various elements of the composition to obtain the effect of the present application, various compositions were prepared. The pH of the composition was adjusted to the stipulated value using salicylic acid, phosphoric acid, or NaOH. The efficacy of the compositions against Feline Calici Virus was determined in the prEN 16777 Wipe test. The log reduction at 2 minutes contact time is presented in the following table, together with the composition of the samples.

| Tradename | chemical name | According to the application 1 | pH outside range A | no APG B | no chelant C | no alkylether carboxylic acid D | quaternary ammonium compound E |
|---|---|---|---|---|---|---|---|
| Water | Water | 93.37% | 93.18% | 93.59% | 93.69% | 93.42% | 90.67% |
| Akypo LF4 | Alkyl Ether Carboxylic Acid | 0.68% | 0.68% | 0.68% | 0.68% | | 0.68% |
| Benzyl Alcohol | Benzyl Alcohol (solvent) | 3.30% | 3.30% | 3.30% | 3.30% | 3.30% | 3.30% |
| Hydrogen Peroxide 35% | Hydrogen Peroxide | 0.50% | 0.50% | 0.50% | 0.50% | 0.50% | 0.50% |
| Triton CG-110 | Alkylpolyglucoside | 0.36% | 1.20% | | 0.36% | 0.36% | 0.36% |
| Mackamine 654 | N,N-Dimethyldecylamine N-oxide | 0.75% | 0.75% | 0.75% | 0.75% | 0.75% | 0.75% |
| Dequest LC 2010 | 1-Hydroxyl ethylidene-1,1,-diphosphonic acid | 0.24% | 0.24% | 0.24% | | 0.24% | 0.24% |
| Bardac 2240 | Didecyldimonium Chloride (Quaternary ammonium surfactant) | | | | | | 2.00% |

-continued

| Tradename | chemical name | According to the application 1 | pH outside range A | no APG B | no chelant C | no alkylether carboxylic acid D | quaternary ammonium compound E |
|---|---|---|---|---|---|---|---|
| pH | | 2.0 | 4.0 | 2.0 | 2.0 | 2.0 | 2.0 |
| Log reduction FCV 2 minutes contact time prEN 16777 Wipe test | | >3.5 | 0.4 | 1.7 | 1.9 | 1.2 | 1.1 |

As can be seen from the table, the composition according to the application shows a log reduction of Feline Calici Virus in the prEN 16777 Wipe test after two minutes contact time of more than 3.5. The indication "more than" means that a specific value cannot be determined as all virus particles have been reduced above the cytotoxicity of the composition for the host cells, which results in a "complete kill". In contrast, the compositions which do not meet all requirements show a log reduction of Feline Calici Virus in the prEN 16777 Wipe test after two minutes contact time of less than 2.0.

More specifically, composition A has a pH of 4.0, which is outside the claimed range of 1.0-3.0. It shows a log reduction of 0.4. It is noted that this composition contains more alkylpolyglucoside than the other samples. This was necessary to obtain a stable, clear solution at pH 4.0. This additional amount would be expected to increase the efficacy, but this is not shown.

Composition B contains no alkylpolyglucoside, and shows a log reduction of 1.7.

Composition C contains no chelating agent, and shows a log reduction of 1.9. Composition D contains no alkylethercarboxylic acid, and shows a log reduction of 1.2.

Composition E contains the elements of the present application and additionally contains 2 wt. % of quaternary ammonium surfactant. This composition shows a log reduction of 1.1.

Example 2: Effect of Different Types of Solvents

The effect of different types of solvents was investigated by preparing and testing a number of further compositions in the manner described in example 1. Again, the pH of the compositions was adjusted to the stipulated value using salicylic acid, phosphoric acid, or NaOH.

| Tradename | chemical name | 1 | 2 | 3 | 4 |
|---|---|---|---|---|---|
| Water | Water | 93.37% | 93.22% | 90.55% | 93.23% |
| Akypo LF4 | Alkyl Ether Carboxylic Acid | 0.68% | 0.68% | 0.68% | 0.68% |
| Benzyl Alcohol | Benzyl Alcohol (solvent) | 3.30% | | | |
| Dowanol PnB | Propylene glycol n-butylether (solvent) | | 3.30 | 6.00 | |
| Dowanol DPnB | Dipropylene glycol n-butylether (solvent) | | | | 3.30 |
| Hydrogen Peroxide | Hydrogen Peroxide | 0.50% | 0.50% | 0.50% | 0.50% |
| Triton CG-110 | Alkylpolyglucoside | 0.36% | 0.36% | 0.36% | 0.36% |
| Mackamine 654 | N,N-Dimethyldecylamine N-oxide | 0.75% | 0.75% | 0.75% | 0.75% |
| Dequest LC 2010 | 1-Hydroxyl ethylidene-1,1,-diphosphonic acid | 0.24% | 0.24% | 0.24% | 0.24% |
| pH | | 2.0 | 2.0 | 2.0 | 2.0 |
| Log reduction FCV 2 minutes contact time prEN 16777 Wipe test | | >3.5 | 2.5 | >3.3 | 3.0 |

It can be seen that all tested solvents show good virucidal properties against Feline Calici Virus in the prEN 16777 Wipe test after two minutes contact time.

The invention claimed is:
1. Water-based virucidal composition suitable for disinfecting a surface contaminated with non-enveloped virus, wherein the composition comprises
    alkylpolyglycoside surfactant in an amount of 0.1-5 wt. %,
    amineoxide surfactant in an amount of 0.1-5 wt. %, wherein the amineoxide is a compound of the formula $R_1R_2R_3N^+O^-$, wherein $R_1$ contains 8 to 18 carbon atoms and $R_2$ and $R_3$ each contain 1-4 carbon atoms, alkylethercarboxylic acid surfactant in an amount of 0.1-5 wt. %, wherein the alkylethercarboxylic acid surfactant is an alkylethercarboxylic acid of the formula R—O—(CH(Y)—CH$_2$—O)$_n$—CH$_2$—COOH, wherein R is an alkyl or alkylene group containing 6-16 carbon atoms, and each Y is independently selected from H or CH$_3$, n is 3-10, or a salt thereof, hydrogen peroxide in an amount of 0.1-7 wt. %, chelating agent in an amount of 0.01-2.0 wt. %, the composition having a pH in the range of 1.0-3.0, wherein the composition comprises less than 15 wt. % of C1-C6 alcohol, less than 0.10 wt. % of quaternary ammonium surfactants, and less than 0.1 wt. % amide surfactants.

2. Composition according to claim 1, wherein the alkylpolyglycoside surfactant is a compound of the formula

where G is a reducing saccharide moiety containing 5 or 6 carbon atoms, R' is a straight chain or branched alkyl or alkylene group having 6 to 20 carbon atoms, and x represents the number of monosaccharide repeating units in the polyglycoside, wherein x is in the range of 1 to 8.

3. Composition according to 1, wherein the amineoxide surfactant is a C8-C16 amineoxide surfactant with R2 and R3 being C1 or C2.

4. Composition according to claim 1, wherein the alkylethercarboxylic acid surfactant is selected from the group consisting of:

compounds in which Y is H, R is a straight chain C6-C12 alkyl and n is 3-8;

compounds wherein R is a straight chain C6 alkyl and n is 3-8;

compounds wherein R is a straight chain C8 alkyl and n is 5-8, and salts thereof, and combinations thereof.

5. Composition according to claim 1, wherein the composition comprises 0.1-5 wt. % of hydrogen peroxide.

6. Composition according to claim 1, wherein the chelating agent is an organophosphonic acid derivative.

7. Composition according to claim 1, wherein the composition comprises less than 15 wt. % of C1-C6 alcohol.

8. Composition according to claim 1, the composition being substantially free of quaternary ammonium surfactants.

9. Composition according to claim 1, which comprises a solvent in an amount of 0.1-10 wt. %.

10. Composition according to claim 9, wherein the solvent is selected from the group consisting of aromatic alcohols and glycolethers.

11. Composition according to claim 1, which is substantially free from Triclosan, parachlorometaxylenol, biguanidines, chlorine bleach, and hypochlorous acid.

12. Composition according to claim 1, wherein the composition does not contain biocidally effective amounts of biocidally active compounds other than the alkylpolyglycoside surfactant, the amineoxide surfactant, the alkylethercarboxylic acid surfactant, the hydrogen peroxide, and the chelating agent, and other than an optical organic solvent.

13. Composition according to claim 1, wherein the composition comprises an active system which consists essentially of the alkylpolyglycoside surfactant, the amineoxide surfactant, wherein the amineoxide is a compound of the formula R1R2R3N+O−, wherein R1 contains 8 to 18 carbon atoms and R2 and R3 each contain 1-4 carbon atoms, the alkylethercarboxylic acid surfactant which is an alkylethercarboxylic acid of the formula R—O—(CH(Y)—CH$_2$—O)$_n$—CH$_2$—COOH, wherein R is an alkyl or alkylene group containing 6-16 carbon atoms, and each Y is independently selected from H or CH$_3$, n is 3-10, or a salt thereof, the hydrogen peroxide, the chelating agent, and optionally solvent, wherein the term active system refers to all elements of the composition which influence the virucidal performance of the composition, as is evidenced by a change in a log reduction in prEN 16777 wipe test against Feline Calici Virus at two minutes contact time of more than 0.5.

14. Composition according to claim 1, which consists essentially of water the alkylpolyglycoside surfactant in an amount of 0.1-5 wt. %, the amineoxide surfactant in an amount of 0.1-5 wt. %, wherein the amineoxide is a compound of the formula R1R2R3N+O−, wherein R1 contains 8 to 18 carbon atoms and R2 and R3 each contain 1-4 carbon atoms, the alkylethercarboxylic acid surfactant in an amount of 0.1-5 wt. % alkylethercarboxylic acid surfactant wherein the alkylethercarboxylic acid surfactant is an alkylethercarboxylic acid of the formula R—O—(CH(Y)—CH$_2$—O)$_n$—CH$_2$—COOH, wherein R is an alkyl or alkylene group containing 6-16 carbon atoms, and each Y is independently selected from H or CH$_3$, n is 3-10, or a salt thereof, the hydrogen peroxide in an amount of 0.1-7 wt. %, the chelating agent in an amount of 0.01-2.0 wt. %, optionally solvent optionally one or more compounds selected from corrosion inhibitors, wetting agents, fragrances, emulsifiers, hydrotropes, thickening agents, coloring agents, preservatives, and anti-foaming agents, less than 15 wt. % of C1-C6 alcohol, less than 0.10 wt. % of quaternary ammonium surfactants, and less than 0.1 wt. % amide surfactants, the composition having a pH in the range of 1.0-3.0.

15. Composition according to claim 1, which shows a log reduction in prEN 16777 wipe test against Feline Calici Virus at two minutes contact time of at least log 2.5.

16. Composition according to claim 1, which does not leave a biocidal or biostatic residue, wherein leaving a biostatic residue is defined as follows: If 6 hours after use of the composition the dried surface is able to kill germs to a minimum reduction of log 3 after contacting the surface with *E. coli, S. aureus, S. typhimurium, P. aeruginosa,* and *E. hirae* a biostatic residue is present.

17. Wet wipe comprising the composition of claim 1.

18. Method for disinfecting a surface suspected to be contaminated with non-enveloped virus, wherein the surface is contacted with the composition according to claim 1, for a contact time of at most 5 minutes.

19. Method according to claim 18, wherein the non-enveloped virus is selected from norovirus, adenovirus, and rhinovirus.

20. Method according to claim 18, wherein the composition is present in a wet wipe.

* * * * *